United States Patent [19]

Kishimoto et al.

[11] Patent Number: 4,994,605

[45] Date of Patent: Feb. 19, 1991

[54] METHOD OF SEPARATING ALPHA-L-ASPARTYL-L-PHENYLALANINE METHYL ESTER THROUGH CRYSTALLIZATION

[75] Inventors: Shinichi Kishimoto, Yokkaichi; Katsumi Sugiyama, Yokosuka, both of Japan

[73] Assignee: Ajinomoto Co., Inc., Tokyo, Japan

[21] Appl. No.: 342,894

[22] Filed: Apr. 25, 1989

Related U.S. Application Data

[63] Continuation of Ser. No. 612,000, May 18, 1984, abandoned.

[30] Foreign Application Priority Data

Jun. 8, 1983 [JP] Japan .................. 58-102327

[51] Int. Cl.$^5$ ........................... C07C 103/52
[52] U.S. Cl. ..................... 562/445; 560/40; 560/41
[58] Field of Search .............. 560/40, 41; 562/445

[56] References Cited

U.S. PATENT DOCUMENTS

3,901,871 8/1975 Anderson .............. 260/112.5 R
4,394,308 7/1983 Sampathkumar et al. ... 260/112.5 R

FOREIGN PATENT DOCUMENTS

1309605 3/1973 United Kingdom .

OTHER PUBLICATIONS

Vogel et al., *A Textbook of Practical Organic Chemistry*, 3rd ed. Longmans, Green and Co., N.Y. 1956, pp. 122–131.
*The Merck Index*, 9th ed. Merck and Co. Inc., Rahway, N.J., U.S.A., 1976, Entry No. 7644, p. 1017.

*Primary Examiner*—Ronald W. Griffin
*Attorney, Agent, or Firm*—Oblon, Spivak, McClelland, Maier & Neustadt

[57] ABSTRACT

A method for crystallizing alpha-L-aspartyl-L-phenylalanine methyl ester (APM) is disclosed. The APM is crystallized from a $C_1$–$C_3$-alcohol/water solution (30–80:70–20 (v/v)). The ester crystallized by (i) concentrating the solution, (ii) cooling the solution, (iii) adjusting the water:alcohol ratio, or (iv) a combination thereof.

20 Claims, 2 Drawing Sheets

○ DATA PROVIDED IN SPECIFICATION
● NEW DATA PROVIDED HEREWITH

METHOD OF SEPARATING ALPHA-L-ASPARTYL-L-PHENYLALANINE METHYL ESTER THROUGH CRYSTALLIZATION

This is a continuation of application Ser. No. 06/612,000, filed on May 18, 1984, now abandoned.

Field of the Invention

This invention relates to a method of separating α-L-aspartyl-L-phenylalanine methyl ester through crystallization.

α-L-aspartyl-L-phenylalanine methyl ester (hereinafter abbreviated as "APM") is a substance of much promise as a new, low-calory sweetener because of the agreeable sweetness it assumes.

BACKGROUND OF THE INVENTION

Typical processes for the manufacture of APM on an industrial scale are: Condensation of N-protected-L-aspartic acid anhydride with L-phenylalanine methyl ester in an organic solvent, followed by removal of the protecting group (U.S. Pat. No. 3,786,039); Direct condensation of a strong-acid addition salt of L-aspartic acid anhydride with L-phenylalanine methyl ester (Jap. Pat. Appln. tokkosho No. 49-14217); and Condensation of N-protected-L-aspartic acid and L-phenylalanine methyl ester in the presence of an enzyme, followed by removal of the protecting group (Jap. Pat. Appln. tokkosho No. 55-135,595).

Industrial production of APM would require a purification step to remove any impurities derived from reactants and by-products, whether the processes described above or any other processes are used. APM may be transferred from the preceeding step to this purification step in the form of a solution, or crude crystals of APM are to be made in solution in this purification step for resin treatment or recrystallization.

The problem was that a large quantity of solvent is required to dissolve APM because it is only slightly soluble in most solvents. For example, its solubility in water at 30° C. is 1 wt %, meaning that 99 Kg water must be used to dissolve 1 Kg of APM; the solubility in pure methanol at room temperature is 1 wt %, and that in pure ethanol is 0.4 wt %.

Solubility increases with increasing temperature; however, since APM undergoes decomposition at elevated temperatures, the highest possible solubility practically attainable is 4 to 5 wt % (at 60° to 70° C.) with the aqueous system.

As a result, a huge volume of APM solution is to be treated and, therefore, very large scale equipments, including piping system, for purification step, as compared with the output of the final product.

Furthermore, APM, if once dissolved, must be isolated from the solution as the final product through crystallization by cooling or other methods. The utility loads required for this process are accordingly very large, providing another disadvantages in commercial operation.

The present inventors' assiduous research to solve these disadvantages associated with conventional processes led them to make the unexpected discovery as described below.

It has been found that the solubility of APM in a mixed solvent of water and a lower alcohol is outstandingly higher than in water or in that lower alcohol alone, if the mixing ratio and temperature are properly selected, and that at low temperatures its solubility in such a mixed solvent is nearly the same as that in water.

In a methanol/water solvent, for example, the solubility of APM, if the mixing ratio and temperature are properly selected, is two to four or more times as large as that in methanol or water alone at the same temperature. What is more surprising is the fact that its solubility in such a mixed solvent is nearly the same as that in water at temperatures lower than 10° C.

The relationship of the solubility of APM in the methanol/water and ethanol/water solvents versus mixing ratio and temperature are illustrated in FIGS. 1 and 2, respectively.

The present inventors have applied these findings to the dissolution (Dissolution herein means not only the dissolving of a solid in a liquid phase, but also the maintaining of the dissolved solid in the solution state.) and crystallization steps in the APM manufacturing process, and succeeded in significantly enhancing productivity per unit space of the entire equipments, or increasing product yields by minimizing thermal decomposition of APM during dissolution.

SUMMARY OF THE INVENTION

The present inventors now provide a process for dissoling and crystallizing APM with extremely high productivity, in which a mixture of water and a lower alcohol is used as solvent, thereby significantly decreasing the volume of solution to be treated; the dissolution temperature is maintained at a relatively low level, thereby reducing decomposition of APM to a minimum; APM is allowed to crystallize from said solution by suitable means, for example, by cooling it through direct or indirect contact with a coolant, by cooling and/or concentrating it through evaporation of solvent, or changing the composition of the mixed solvent by addition of water or a lower alkanol; and the crystals of APM thus obtained are collected by suitable means.

DESCRIPTION OF THE PREFERRED EMBODIMENTS

The lower alcohols used in the process of this invention should preferable have a carbon number not exceeding three. Lower alcohols whose carbon number is four or more (that is, butanol and higher alcohols) have a markedly low solubility in water, causing phase-separation in some cases when mixed with water, and it is therefore difficult to prepare a mixed solvent of proper mixing ratio that assures the intended outstanding effects described above. Of the lower alcohols whose carbon number is three or less (methanol, ethanol and 1- and 2-propanols), methanol is most preferable, because it avoids possible ester exchange of the methyl group of APM during dissolution encountered with other alcohols.

The mixing ratio of the lower alcohol and water, that is, the composition of the mixed solvent, may be selected in the range within which the intended effects of this invention can be conspicuously exhibited, that is, APM can be more efficiently crystallized and separated in larger quantities than when the same amount of water is used alone.

In the methanol/water system, for example, the preferred content of methanol is about 30 to 80% by volume. What is to be noticed here is that, when a solution of APM in a methanol/water mixed solvent is cooled without stirring at an initial APM concentration of 2 wt % or higher to form sherbet-like pseudo-solid phase, a change in crystal habit of separated APM takes place at a methanol content of about 50%, yielding raphides in the range of 0 to 50% and needles in the range of 50 to 80%. Thus the process of this invention can be advantageously used not only for purification of APM, but also as a crystal habit changing method to meet specific end uses.

Since APM is unstable at high temperatures as described earlier, it is preferable that all the operations in the process of this invention be carried out at temperatures of about 60° C. or lower.

Any cooling method may be used in the process of this invention. For indirect cooling, the heat conduction system or the convective heat transfer system with mechanical stirring may be employed. As an example of direct cooling may be mentioned a method of evaporating the solvent under reduced pressure, thereby the solution is cooled by the latent heat of vaporization. When the solution is cooled by direct contact with a coolant, it is preferable to use nontoxic coolant such as propylene glycol, because the major use of APM is as a sweetener and the process of this invention is employed as the final step of its manufacturing process. If the evaporation method is applied to a mixed solvent containing 60% by volume or less of a lower alcohol, distillation of the alcohol will proceed preferentially; as a result, a high yield of APM can be achieved by the combined effects of concentration and change in solvent composition.

Furthermore, with mixed solvent systems of certain compositions, it will be advantageous to add cold water to the solution, thereby crystallization is caused by the combined effects of temperature depression and change in solvent composition. Similarly, it is also possible to decrease the solubility of APM by addition of a lower alcohol in some cases. These can easily be understood from the solubility curves shown in FIGS. 1 and 2.

In any of the methods described above, use of a water/lower alcohol mixture as solvent significantly reduces the volume of solution to be treated. This, combined with the lower specific heat and latent heat of vaporization than with the aqueous system, markedly reduces the energy loads of utilities required for heating and cooling, thus providing great advantages in industrial operation.

The solution of APM in a mixed solvent of water and a lower alcohol, which is to be subjected to the crystallization/separation process of this invention, is normally prepared by dissolving crude APM (for purification or crystal habit conversion) or purified APM (for crystal habit converion) in fresh water and lower alcohol. However, such a solution of APM, if available at an intermediate step of the APM manufacturing process, may be directly subjected to the process of this invention.

Filtration, centrifugal separation and any other commonly used methods may be employed to separate crystallized APM from the mother liquor.

No disadvantage has been found, compared with the aqueous system, in terms of removal of impurities derived from reactants and by-products. It has been found that some types of impurities can be removed more efficiently by the process of this invention.

The following examples illustrate the process of this invention in more detail.

EXAMPLES

Example 1

A stainless steel crystallizer (capacity: 150 liters) equipped with an agitator and internal coil was charged with 60 liters of industrial methanol (first grade), followed by addition of water to make up 100 liters (methanol content: 60 vol %). The liquid was heated to 60° C. with stirring by passing steam through the coil, and 9.3 Kg of APM containing 0.3% water and 3% impurities was added and dissolved in the mixed solvent. Concentration of APM in the solution is about 9 wt %.

As is apparent from the solubility curve shown in FIG. 1, the system is in an unsaturated condition, and therefore APM readily dissolves completely. Since the solubility of APM in water at the same temperature is 4.2 wt %, it will be easily understood that more than twice the volume of water would be required to dissolve the same amount of APM even at the saturation point.

The solution obtained above was then cooled by introducing a refrigerant of 0° C. through the coil, and the slurry obtained after about two hours was subjected to centrifugal separation. The centrifuge was 24 inches in diameter.

The wet cake was dried, affording 8.4 Kg dry product. Recovery yield: 90%; moisture content: 3%; impurities: 0.5%.

Example 2

A jacketed, stainless-steel, cylindrical vessel 80 mm in internal diameter was used in this example.

A mixture of 0.8 liter methanol and water (total volume: 2 liters) was heated to 50° C., and about 125 g of crude APM (moisture content: 1.5%; impurities: 2.5%) was added to this mixed solvent and dissolved. The concentration of APM is about 6 wt %.

This solution was transferred to the cylindrical vessel mentioned above, and cooled by introducing a refrigerant of 0° C. through the jacket. The solidified sherbet-like content was discharged after 1.5 houts and ground into slurry. It was found that APM is present in the form of raphides through observation under a microscope. The slurry was subjected to centrifugal separation, and the wet cake obtained was dried, yielding about 105 g of pure APM. Recovery yield: 85%; moisture content: 3%; impurities: 0.1%.

The amount of treated APM per unit volume of equipment was about 2.5 times larger than would be the case in which water is used as solvent.

Example 3

Ethanol (first grade reagent; 120 ml) was charged in a 500-ml flask fitted with a stirrer and water was added to make up 200 ml. About 16 g of crude APM (moisture content: 1%; impurities: 5%) was dissolved in this mixed solvent. The concenration of APM is about 8 wt %. The solution was stirred for about one hour while being cooled in an ice bath.

The formed crystals were collected by filtration and dried, giving about 13.5 g of APM. Recovery yield: 86%; moisture content: 3%; impurities: 0.9%. The amount of treated APM per unit volume of equipment (vessel) was about three times greater than would be the case in which water is used as solvent. No α-L-aspartyl-L-phenylalanine ethyl ester was detected in the crystals obtained.

Example 4

Water was added to 120 ml 1-propanol (first grade reagent) to make up 200 ml, the mixture was heated to 50° C., about 16 g of crude APM (moisture content: 1%; impurities: 5%) was dissolved in this mixed solvent, the solution was cooled in an ice bath, and the formed crystals were collected by filtration.

After drying, about 11 g of pure APM was obtained. Recovery yield: 71%; moisture content: 3%; impurities: 0.1%.

Example 5

To a 200 ml solution of APM in a methanol/water mixed solvent (methanol content: 60 vol %; APM concentration: 9 wt %) held at 60° C., was added 100 ml water of 5° C. The methanol content decreased from 60 to about 40 vol %. The liquid temperature immediately after addition of water was about 35° C. Stirring was continued for some time after crystallization of APM took place, and a portion of the mother liquor was taken and analyzed. The APM concentration in the mother liquor was 5.2 wt %. The slurry was cooled in an ice bath for an additional one hour, and the crystals were collected by filtration, giving 16 g of dry APM. Recovery yield: 88%; moisture content: 3%; impurities: 1%.

As is apparent from the foregoing description and examples, application of the process of this invention to the dissolution/crystallization step in an industrial manufacturing process of APM provides markedly greater advantages as listed below over conventional processes using water alone as solvent.

(1) The volume of liquid to be treated when a given amount of APM is dissolved can be significantly reduced, thus greatly enhancing the equipment efficiency, including piping system and other ancillary units, by a factor of 2 to 4 or more.

(2) APM can be dissolved and the resultant solution can be maintained at temperatures 10° to 20° C. lower than with the aqueous system at the same concentration, thereby minimizing decomposition of APM and achieving higher yields of the final product.

(3) Since the volume of APM solution to be treated is significantly reduced and the specific heat of the solution is smaller than in the aqueous system, utility loads required for heating and cooling can be markedly reduced.

Figure 1:
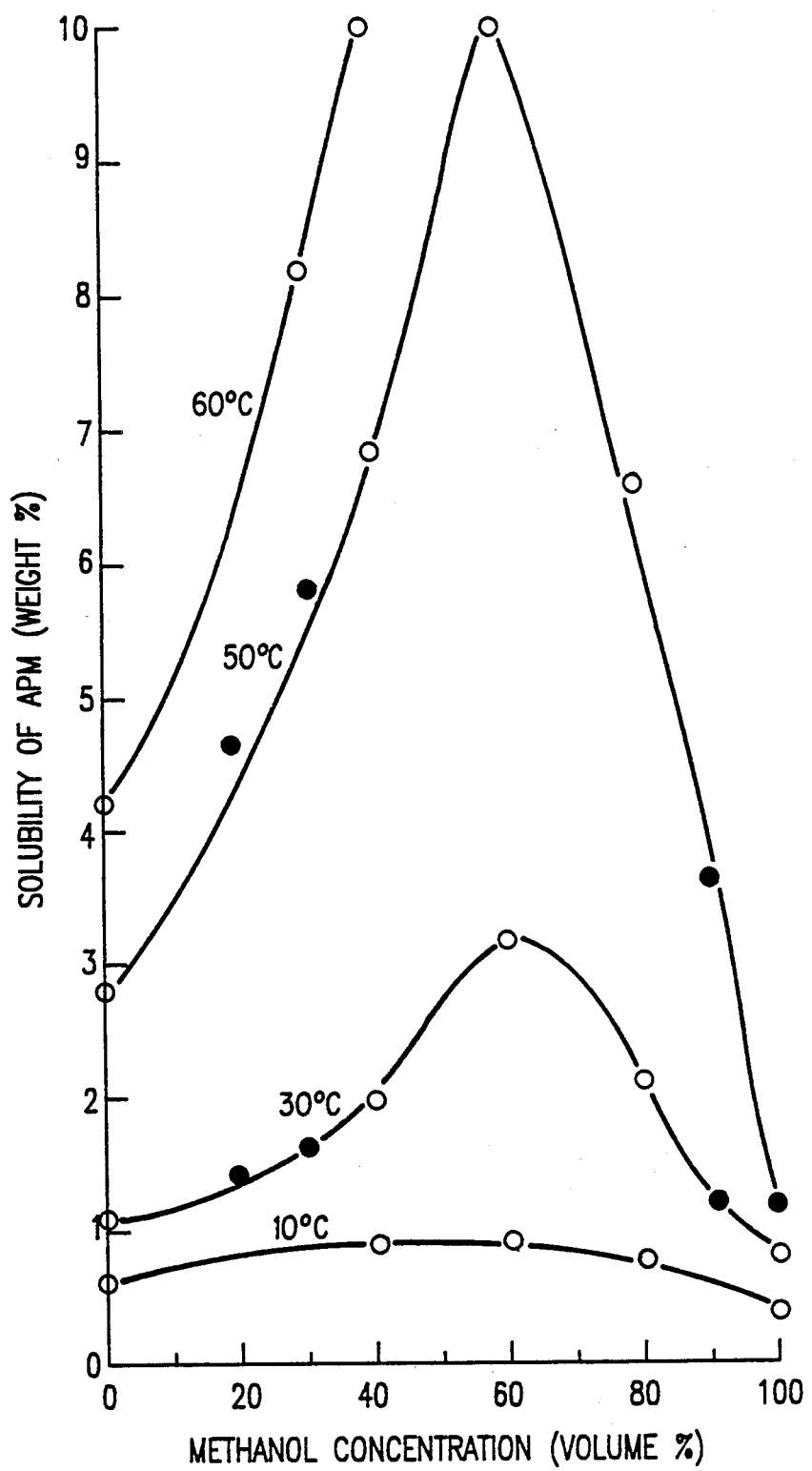
FIG. 1 shows the solubility curve of APM in the methanol/water system.
Figure 2:
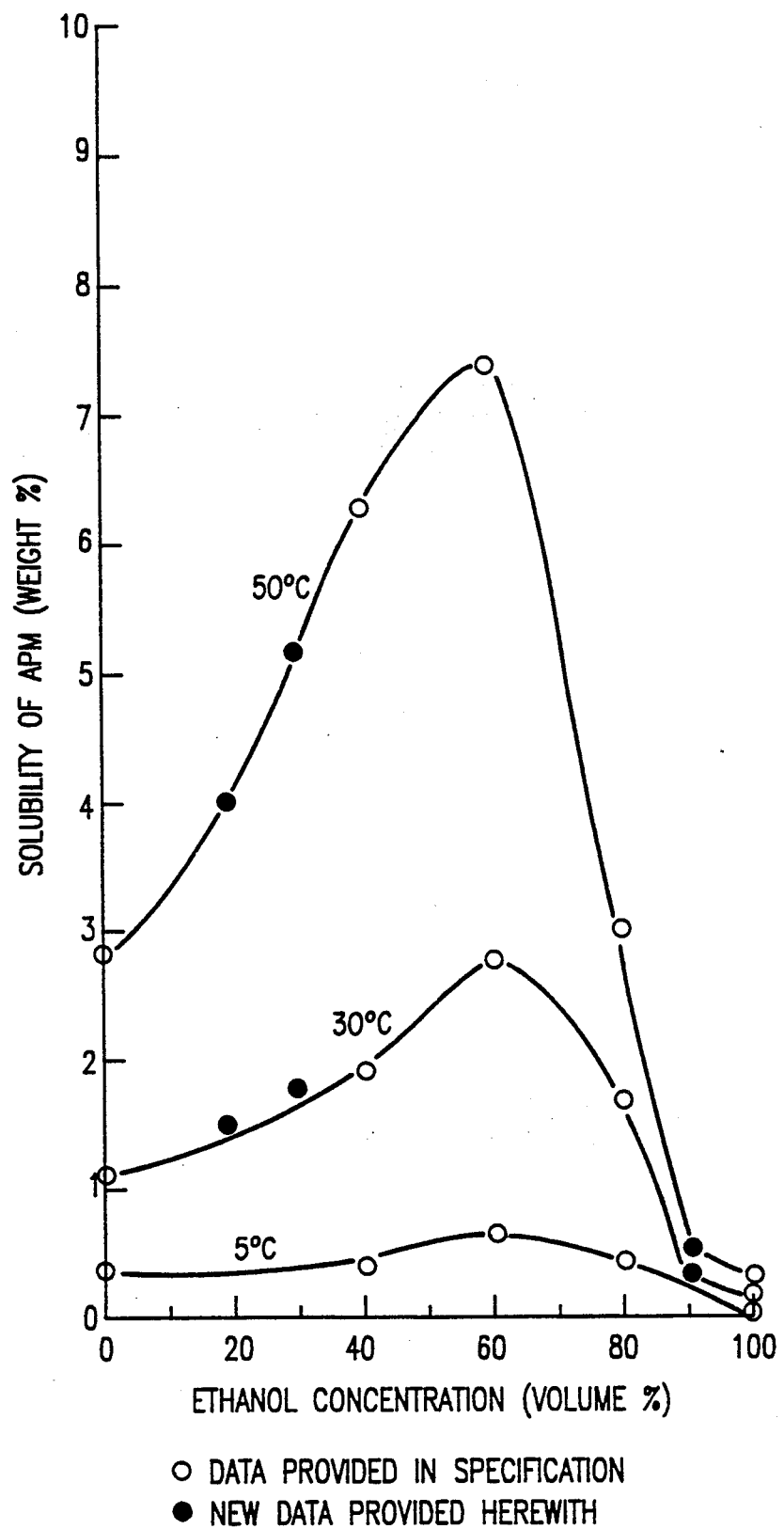
FIG. 2 shows the solubility curve in the ethanol/water system.

What is claimed is:

1. A method of crystallizing α-L-aspartyl-L-phenylalanine methyl ester from a solution containing the ester, comprising:
    (A) adding an already formed α-L-aspartyl-L-phenylalanine methyl ester product to a mixture of water and a $C_{1-2}$ alcohol to dissolve said product in said mixture, wherein said alcohol is present in the water/alcohol mixture in an amount of about 30 to about 80 percent by volume;
    (B) crystallizing the ester by either (B1) concentrating the solution, (B2) cooling the solution to a temperature effective for crystallization, (B3) adjusting the water:alcohol ratio, or (B4) a combination thereof, to prevent formation of crystals of said esters; and
    (C) separating said crystals from the solution.

2. The method of claim 1, comprising carrying out step (A) at a temperature of from 30° C. to 60° C.

3. The method of claim 1, wherein the temperature of the solution prior to step (B) is between about 30° C. and the boiling point of the solvent.

4. The method of claim 1, wherein the temperature of the solution prior to step (C) is not higher than about 30° C.

5. The method of claim 1, wherein the alcohol is methanol.

6. The method of claim 5, wherein the methanol is present in an amount of up to 50 percent by volume of said water/alcohol mixture.

7. The method of claim 1, wherein cooling is accomplished by using a heat conduction system or a convective heat transfer system.

8. The method of claim 1, wherein cooling is accomplished by evaporating the solvent of the solution under reduced pressure.

9. The method of claim 1, wherein cooling is performed by direct contact with a coolant.

10. The method of claim 9, wherein the coolant is propylene glycol.

11. The method of claim 1, wherein the alcohol is present in an amount of up to 60 percent by volume of the water/alcohol mixture, and the solution is concentrated by evaporation.

12. The method of claim 1, wherein cold water is added to the solution in step (B).

13. The method of claim 1, wherein the crystallization of the ester in step (B) is carried out by adding alcohol.

14. The method of claim 1, wherein step (C) is carried out by filtration or centrifugal separation.

15. The method of claim 1, comprising:
    (A) adding an already formed solid alpha-L-aspartyl-L-phenylalanine methyl ester product to said mixture of water and said alcohol.

16. The method of claim 1, comprising:
    (A) adding a solution of an already formed alpha-L-aspartyl-L-phenylalamine methyl ester product to said mixture of water and said alcohol.

17. The method of claim 16, comprising adding said already formed alpha-L-aspartyl-L-phenylalanine methyl ester product to a mixture of water and methanol.

18. The method of claim 16, comprising adding said already formed α-L-aspartyl-L-phenylalanine methyl ester product to a mixture of water and ethanol.

19. The method of claim 1, wherein said alcohol is ethanol.

20. The method of claim 1, comprising adding crude crystals of α-L-aspartyl-L-phenylalanine methyl ester product to said mixture of water and alcohol.

* * * * *